(12) United States Patent
Dvorkin et al.

(10) Patent No.: US 8,938,045 B2
(45) Date of Patent: Jan. 20, 2015

(54) METHOD OF DETERMINING RESERVOIR PROPERTIES AND QUALITY WITH MULTIPLE ENERGY X-RAY IMAGING

(71) Applicant: Ingrain, Inc., Houston, TX (US)

(72) Inventors: Jack Dvorkin, Houston, TX (US); Naum Derzhi, Houston, TX (US); Elizabeth Diaz, Houston, TX (US); Joel Walls, Houston, TX (US)

(73) Assignee: Ingrain, Inc., Houston, TX (US)

( * ) Notice: Subject to any disclaimer, the term of this patent is extended or adjusted under 35 U.S.C. 154(b) by 260 days.

(21) Appl. No.: 13/738,106

(22) Filed: Jan. 10, 2013

(65) Prior Publication Data

US 2013/0182819 A1     Jul. 18, 2013

Related U.S. Application Data

(60) Provisional application No. 61/586,153, filed on Jan. 13, 2012.

(51) Int. Cl.
*G01N 23/20* (2006.01)
*H05G 1/04* (2006.01)
*G01N 23/04* (2006.01)

(52) U.S. Cl.
CPC ........ *G01N 23/046* (2013.01); *G01N 2223/419* (2013.01)
USPC ................. 378/4; 378/5; 378/6; 378/7; 378/8; 378/9; 378/22; 378/23; 378/24; 378/25; 378/26; 378/27; 250/253; 250/255; 250/256; 250/267

(58) Field of Classification Search
USPC .......... 378/4, 5, 6, 7, 8, 9, 22, 23, 24, 25, 26, 378/27; 250/253, 255, 256, 267
See application file for complete search history.

(56) References Cited

U.S. PATENT DOCUMENTS

| 5,063,509 | A | * | 11/1991 | Coles et al. ..................... 702/23 |
| 2009/0274276 | A1 | * | 11/2009 | Wraight et al. .................. 378/89 |
| 2010/0193676 | A1 | * | 8/2010 | Jacobson et al. ........... 250/269.6 |
| 2013/0028371 | A1 | | 1/2013 | Derzhi |
| 2014/0119497 | A1 | * | 5/2014 | Guzman et al. .................. 378/5 |

OTHER PUBLICATIONS

Siddiqui, S., et al., "Dual-Energy CT-Scanning Applications in Rock Characterization," Society of Petroleum Engineers, SPE 90520, Sep. 2004, pp. 1-9.

(Continued)

*Primary Examiner* — Nicole Ippolito
(74) *Attorney, Agent, or Firm* — Kilyk & Bowersox, P.L.L.C.

(57) ABSTRACT

A method of evaluating a reservoir includes a multi-energy X-ray CT scan of a sample, obtaining bulk density and photoelectric effect index effect for the sample, estimation of at least mineral property using data obtained from at least one of a core gamma scan, a spectral gamma ray scan, an X-ray fluorescence (XRF) analysis, or an X-ray diffraction (XRD) analysis of the sample, and determination of at least one sample property by combining the bulk density, photoelectric effect index, and the at least one mineral property (e.g., total clay content). Reservoir properties, such as one or more of formation brittleness, porosity, organic material content, and permeability, can be determined by the method without need of detailed lab physical measurements or destruction of the sample. A system for evaluating a reservoir also is provided.

26 Claims, 10 Drawing Sheets

(56) References Cited

OTHER PUBLICATIONS

Wellington, S.L., et al., "X-Ray Computerized Tomography," Journal of Petroleum Technology, 1987, pp. 885-898.

Modica, C.J., et al., "Estimation of kerogen porosity in source rocks as a function of thermal transformation: Example from the Mowry Shale in the Powder River Basin of Wyoming," AAPG Bulletin, Jan. 2012, V. 96, No. 1, pp. 87-108.

International Search Report and Written Opinion for PCT/US2013/20936, May 14, 2013.

Walls, J.D., et al., "Eagle Ford Shale Reservoir Properties from Digital Rock Physics," First Break, vol. 29, Jun. 2011, pp. 96-101.

Ayyalasomayajula, K.K., et al., "Analysis of Calibration Materials to Improve Dual-Energy CT Scanning for Petrophysical Applications," SPE Technical Conference and Exhibition, vol. 2, Oct. 2011, pp. 1712-1722.

\* cited by examiner

METHOD OF DETERMINING RESERVOIR PROPERTIES AND QUALITY WITH MULTIPLE ENERGY X-RAY IMAGING

This application claims the benefit under 35 U.S.C. §119 (e) of prior U.S. Provisional Patent Application No. 61/586, 153, filed Jan. 13, 2012, which is incorporated in its entirety by reference herein.

BACKGROUND OF THE INVENTION

The present invention relates to a method for characterizing the quality of reservoir rock and more particularly with the use of multiple energy X-ray imaging.

In the petroleum industry, the oil and gas life cycle stages are exploration, appraisal, development, and production. Decisions are made at each of the stages with the overall goal of ensuring the reservoir produce at the maximum production level. At the beginning of the first stage, there are minimal amount of data. As the life cycle continues, different types of reservoir data are collected, such as seismic, well logs, core data, and production data. The analysis and interpretation of the reservoir data is critical to decision making as the life cycle. A major challenge is characterizing the reservoir quality.

Several factors are to be considered in determining where and how to evaluate reservoir quality and complete a gas or oil shale reservoir. Among the most important factors can be: (a) brittleness of the formation which helps assess how easy or difficult it is to create a hydraulically connected fracture network during hydro-fracturing operations; (b) porosity which is the storage capacity, (c) organic material (OM) content and (d) permeability which is the production-driving parameter.

The brittleness is directly related to the mineralogy: the higher the carbonate and quartz content, the more brittle is the rock and, conversely, the higher the clay or OM content, the less brittle (or more ductile) is the rock. The porosity affects the bulk density: the smaller the density, the higher the porosity. Finally, the permeability is often a function of porosity and the grain size and can be assessed from these two numbers.

Currently, only high-quality well log data or detailed lab physical measurements on core samples and mineralogical analysis can help assess these parameters. However, sufficiently detailed lab measurements are time consuming and usually take many weeks to obtain, usually result in destruction of the sample, and can only be done at a few depth locations.

There is a need in reservoir quality evaluation for methods that can estimate reservoir properties such as formation brittleness, porosity, organic material content, and permeability, without need of detailed lab physical measurements on core samples which destroy the sample and can only be done at a few depth locations.

SUMMARY OF THE INVENTION

A feature of the present invention is to provide a method to estimate reservoir properties such as formation brittleness, porosity, organic material content, and permeability, without need of detailed lab physical measurements or destruction of the sample.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method for evaluating a reservoir, comprising (a) performing a multi-energy X-ray CT scan of a sample at a depth interval at two or more different energy levels; (b) obtaining bulk density and photoelectric effect index for the sample using CT values obtained for voxels in the sample from the multi-energy X-ray CT scan; (c) estimating at least one mineral property using data obtained from at least one of a core gamma scan, a spectral gamma ray scan, an X-ray fluorescence (XRF) analysis, or an X-ray diffraction (XRD) analysis of the sample; and (d) determining at least one sample property by combining the bulk density, photoelectric effect index, and the at least one mineral property.

The present invention relates to a method for evaluating a reservoir, comprising (a) performing a multi-energy X-ray CT scan of a sample at a depth interval at two or more different energy levels; (b) obtaining bulk density and photoelectric effect index for the sample using CT values obtained for voxels in the sample from the multi-energy X-ray CT scan; (c) using data of at least one of a gamma ray scan, a spectral gamma ray scan, an X-ray fluorescence (XRF) analysis, or an X-ray diffraction (XRD) analysis of the sample to estimate total clay content; (d) calculating a mineral composition of the sample using the estimate of total clay content and the photoelectric effect index, (e) determining brittleness index of the sample using the mineral composition; (f) determining kerogen and porosity fractions; (g) determining porosity of the sample using the bulk density and the kerogen and porosity fractions; (h) estimating permeability of the sample using the porosity; and (i) determining a reservoir quality index by combining the brittleness index, porosity, and permeability.

Systems for performing the methods are also provided.

It is to be understood that both the foregoing general description and following detailed description are exemplary and explanatory only and are intended to provide a further explanation of the present invention, as claimed.

The accompanying drawings, which are incorporated in and constitute a part of this application, illustrate features of the present invention and together with the description, serve to explain the principles of the present invention.

BRIEF DESCRIPTION OF THE DRAWINGS

In FIGS. 1A-C (and FIGS. 2-5, 6A-B, 8A-B, 9A-C, 10A-C and 11), the depths are shown as normalized values that increase from left-to-right along the x-axis.

DETAILED DESCRIPTION OF THE INVENTION

Figure 1A:
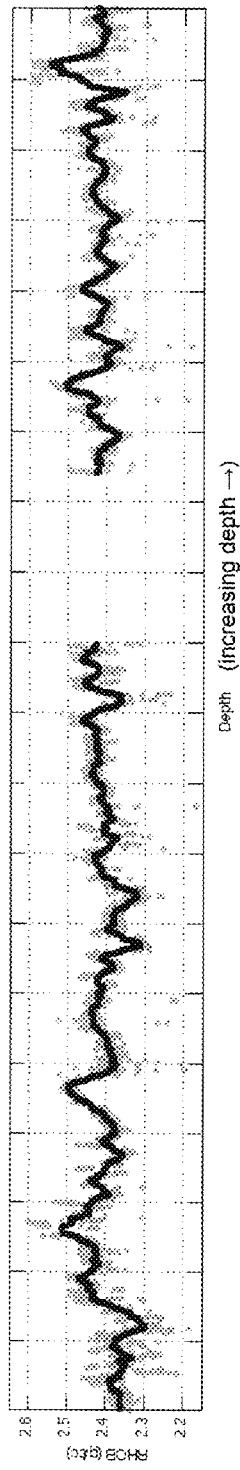
FIGS. 1A-C show depth plots of the multiple energy X-ray imaging-derived bulk density ("RHOB (g/cc)") (FIG. 1A), effective atomic number ("Z Effective") (FIG. 1B), and photoelectric effect index as derived from the effective atomic number according to Equation 1 described herein ("PEF") (FIG. 1C), for a core under examination according to an example of the present application. Grey dots represent high-resolution logs, whereas solid dots represent the same data smoothed in depth (50-point mean running window).

The present invention relates to methods for evaluating reservoir quality which can estimate reservoir properties, such as one or more of formation brittleness, porosity, organic material content, and permeability, without need of detailed lab physical measurements or destruction of the sample. To solve and avoid problems of needing to rely on high-quality well log data and detailed lab analyses for reservoir evaluation, multiple energy X-ray imaging technology is used to provide bulk density and photo electric effect (PEF) inputs for use in methods of the present application. Multiple energy X-ray imaging technology is described by Derzhi in U.S. patent application Ser. No. 13/527,660, which is incorporated in its entirety by reference herein. Multiple energy X-ray imaging can be applied to a core or, where a core is not available, to drill cuttings, plugs or other types of samples. Multiple energy X-ray imaging provides two outputs which are the bulk density and the photoelectric effect index. The latter (photoelectric effect index) is mostly driven by the mineralogy and is sometimes converted to effective atomic number (Zeff). Multiple energy X-ray imaging is rapid and has high vertical or lateral resolution, plus it can be combined with other rapid scan data such as core gamma ray (GR) and/or spectral gamma ray (SGR) data, or using data of other sources such as X-ray fluorescence (XRF) or X-ray diffraction (XRD) analysis data, to add another dimension to the analysis of reservoir quality.

Specifically, by having GR- and/or SGR-based estimates of the total clay content or specific clay and other mineral types, this information can be included into the mineral balance equation. This allows estimation of the mineral composition, including (but not limited to) at least three minerals (e.g., calcite, quartz, and illite). Where SGR provides a detailed mineral count, the multiple energy X-ray imaging PEF data can be resolved for more than three mineral constituents. Such detailed mineralogy assessment can lead to a better brittleness estimate. It can be also instrumental in increasing the precision of multiple energy X-ray imaging-bulk density-to-porosity and kerogen content transform. It also can help make more accurate permeability estimates as different mineralogies (especially in clay) imply different grain size, a parameter crucial in a porosity-to-permeability transform. Though methods of the present application are illustrated herein wherein the three minerals are calcite, quartz, and illite, the methods herein are not limited to that particular combination of minerals and can be applied to other minerals and combinations thereof.

PEF can be used to obtain mineralogy by scaling it between two end members, e.g., calcite and quartz plus clay. To add the missing second equation, the ratio between two or more contrasting materials, such as clay and non-clay minerals, can be used. This can be done, for example, by analyzing the relevant SEM (scanning electron microscope) images or using GR data obtained on the core or cuttings, or other sources.

Once the mineralogy is determined, the brittleness index can be determined, which, for example, can be high where there is less clay or OM and low where there is more clay or OM. The determining of the brittleness index can comprise, for example, determining the brittleness index from elastic properties of the solid calculated from the mineral composition. The brittleness index can be in positive relationship to Young's modulus and Poisson's ratio. The brittleness index can be in positive linear relationship to Young's modulus and Poisson's ratio.

Next, by using the multiple energy X-ray imaging bulk density, for example, the porosity can be determined by assuming the proportion between the kerogen and porosity. This can be done, for example, by analyzing SEM images or relating the kerogen content to radioactive mineral content. From SEM or FIB-SEM, for example, porosity and organic content can be obtained, but usually the obtained organic content is more reliable. In view thereof, organic content can be used to calculate porosity. The reverse can be done with calculation of the organic content by using the porosity from the SEM or FIB-SEM. It can also be based on experience with various shale formations or on thermal kerogen conversion models (See, e.g., Modica, C. J. et al., AAPG Bulletin, January 2012, v. 96 no. 1, pp. 87-108). Organic content of the sample also can be determined using other methods, such as CT scan, pyrolysis, Fourier Transform Infrared spectroscopy (FTIR), and/or other methods.

Next, the porosity thus determined can be used to estimate the permeability. The grain size, pore size, or specific surface area, can come, for example, from 2D SEM images of samples or 3D FIB (focused ion beam)-SEM images of samples or selected portions of samples. The SEM imaging can be done, for example, on a face of a sample.

Finally, by combining the brittleness index, porosity, and permeability, a reservoir quality index can be determined, which can be high for high brittleness, porosity, and permeability and low where these three parameters are small.

An alternative method can include the use of data provided by spectral gamma scanning tools. Using this data, in particular, the ratio of thorium (Th) and potassium (K), the fractions of illite and kaolinite can be calculated, and also total clay fraction in the core, and this value can be used instead of assuming a relationship between quartz and illite fractions. An alternative method can include use of data provided by X-ray fluorescence (XRF) analysis or X-ray diffraction (XRD) analysis, which is used in place of or in addition to gamma ray or spectral gamma scans for clay content and other minerals.

An alternative method is to use either existing or newly obtained relation (if such a relation exists based on physical or numerical experiments) between the bulk density and TOC or any elemental content (e.g., uranium) and TOC to compute TOC from the abovementioned inputs.

Multiple energy X-ray imaging methods can be used herein to obtain bulk density (RhoB) and photoelectric effect index (Pef) from multiple energy scans of the sample, e.g., high and low energy, CT values, which calculated values of bulk density and Pef can be used in methods of the present application such as described herein. Multiple energy X-ray imaging methods which can be used to obtain bulk density and effective atomic number or Pef are described, for example, by Wellington, S. L. et al., "X-ray Computerized Tomography," JOURNAL OF PETROLEUM TECHNOLOGY, 1987); Siddiqui, A. et al., "Dual-Energy CT-Scanning Applications in Rock Characterization," SOCIETY OF PETROLEUM ENGINEERS, 2004, SPE 90520; and U.S. patent application Ser. No. 13/527,660, which are incorporated in their entireties by reference herein. The general steps in a method of analysis using multiple energy X-ray imaging methods to obtain bulk density and effective atomic number include but are not limited to i) performing a scan (such as a dual energy X-ray CT scan) of the target object, and ii) calculating density and effective atomic number for the target object, based on the high and low energy CT values.

The additional description below may use a complete well core sample (e.g. whole core or round core) as an example of the target object, but it is to be understood that the methods described herein apply not only to whole core samples but to slabbed cores, cut or sliced cores, plugs, drill cuttings, rock samples generally and to porous bodies in general. The types of rock to which a method of the present invention can be applied are not necessarily limited to shale. The rock sample can be, for example, organic mud rock, shale, carbonate, sandstone, limestone, dolostone, other porous rocks, or any combinations thereof.

The present invention includes the following aspects/embodiments/features in any order and/or in any combination:

1. The present invention relates to a method of evaluating a reservoir, comprising:
   (a) performing a multi-energy X-ray CT scan of a sample at a depth interval at two or more different energy levels;
   (b) obtaining bulk density and photoelectric effect index for the sample using CT values obtained for voxels in the sample from the multi-energy X-ray CT scan;
   (c) estimating at least one mineral property using data obtained from at least one of a core gamma scan, a spectral gamma ray scan, an X-ray fluorescence (XRF) analysis, or an X-ray diffraction (XRD) analysis of the sample; and
   (d) determining at least one sample property by combining the bulk density, photoelectric effect index, and the at least one mineral property.

2. The method of any preceding or following embodiment/feature/aspect, wherein the at least one mineral property comprises total clay content.

3. The method of any preceding or following embodiment/feature/aspect, further comprising performing a core gamma scan or a spectral gamma ray scan on the sample prior to step (c).

4. The method of any preceding or following embodiment/feature/aspect, wherein the estimating of the at least one mineral property comprises using data of at least one of a gamma ray or a spectral gamma ray scan of the sample to estimate total clay content, and calculating a mineral composition of the sample using the estimate of total clay content and the photoelectric effect index.

5. The method of any preceding or following embodiment/feature/aspect, further comprising determining brittleness index of the sample using the mineral composition.

6. The method any preceding or following embodiment/feature/aspect, wherein the determining of the brittleness index comprises determining the brittleness index from elastic properties of the solid calculated from the mineral composition.

7. The method any preceding or following embodiment/feature/aspect, wherein the brittleness index is in positive relationship to Young's modulus and Poisson's ratio of the solid.

8. The method any preceding or following embodiment/feature/aspect, wherein the brittleness index is in positive linear relationship to Young's modulus and Poisson's ratio of the solid.

9. The method of any preceding or following embodiment/feature/aspect, further comprising:
   using an organic content obtained for the sample and bulk density and mineral composition to calculate porosity.

10. The method of any preceding or following embodiment/feature/aspect, wherein obtaining the organic content of the sample comprises determining the organic content using SEM, CT scan, pyrolysis, FTIR, or FIB-SEM.

11. The method of any preceding or following embodiment/feature/aspect, further comprising:
    a) obtaining grain size, pore size, or specific surface area; and
    b) calculating permeability using porosity or grain size or pore size or specific surface area.

12. The method of any preceding or following embodiment/feature/aspect, further comprising calculating a reservoir quality index using brittleness and porosity.

13. The method of any preceding or following embodiment/feature/aspect, further comprising calculating a reservoir quality index using brittleness, porosity, and permeability.

14. The method of any preceding or following embodiment/feature/aspect, wherein the sample is a core.

15. The method of any preceding or following embodiment/feature/aspect, wherein the sample is a set of drill cuttings.
16. The method of any preceding or following embodiment/feature/aspect, wherein the sample is a plug.
17. The present invention relates to a method for evaluating a reservoir, comprising:
  (a) performing a multi-energy X-ray CT scan of a sample at a depth interval at two or more different energy levels;
  (b) obtaining bulk density and photoelectric effect index for the sample using CT values obtained for voxels in the sample from the multi-energy X-ray CT scan;
  (c) using data of at least one of a gamma ray scan, a spectral gamma ray scan, an X-ray fluorescence (XRF) analysis, or an X-ray diffraction (XRD) analysis of the sample to estimate total clay content;
  (d) calculating a mineral composition of the sample using the estimate of total clay content and the photoelectric effect index;
  (e) determining brittleness index of the sample using the mineral composition;
  (f) determining kerogen fraction;
  (g) determining porosity of the sample using the bulk density, mineral composition, and the kerogen fraction;
  (h) estimating permeability of the sample using the porosity and grain size, pore size, or specific surface area; and
  (i) determining a reservoir quality index by combining the brittleness index, porosity, and permeability.
18. The method of any preceding or following embodiment/feature/aspect, wherein reservoir quality index is in positive numerical relationship with the brittleness index, porosity, and permeability.
19. The method of any preceding or following embodiment/feature/aspect, wherein the determining of the mineral composition of the sample using the photoelectric effect index comprises scaling the photoelectric effect index as a linear interpolation between first and second mineralogical end members of the sample, wherein the first mineralogical end member is a mixture of a first mineral and a second mineral wherein the first mineralogical end member has a $P_e$ which is $P_{e1}$, and the second mineralogical end member is a third mineral which has a $P_e$ which is $P_{e2}$, wherein a volume fraction $f_1$ of the first mineralogical end member in a mineral mixture of the sample is calculated as $f_1=(P_{e2}-P_e)/(P_{e2}-P_{e1})$.
20. The method of any preceding or following embodiment/feature/aspect, wherein the first, second, and third minerals are different minerals from each other.
21. The method of any preceding or following embodiment/feature/aspect, wherein the first mineral is quartz, the second mineral is illite, and the third mineral is calcite.
22. The method of any preceding or following embodiment/feature/aspect, wherein the fraction of quartz in the first mineralogical end member is $f_{Q1}$ and the fraction of illite is $f_{I1}=1-f_{Q1}$, and wherein volume fractions of the first mineral, the second mineral, and the third mineral in the sample as an entirety are calculated respectively as $f_Q=f_{Q1}f_1$, $f_I=(1-f_{Q1})f_1$, $f_C=1-f_1$, wherein $f_Q+f_I+f_C$ is 1.
23. The method of any preceding or following embodiment/feature/aspect, wherein the determining of the porosity $\phi$ of the sample is calculated as $\phi=[\rho_s-\rho_b-X_k(\rho_s-\rho_k)]/\rho_s$, $\rho_b=X_s\rho_s+X_k\rho_k$, where $X_s$ is volume fraction of solid mineral in the entire sample and $X_k$ is volume fraction for kerogen in the entire sample and $X_s+X_k+\phi=1$, wherein measure bulk density $\rho_b$ is determined as $\rho_b=X_s\rho_s+X_k\rho_k$, wherein $\rho_s$ is density of the solid phase and $\rho_k$ is density of kerogen.
24. The method of any preceding or following embodiment/feature/aspect, wherein the sample is a core or drill cuttings.
25. A system for evaluating a reservoir, comprising:
  (a) a multi-energy X-ray CT scanner having a stage capable of holding a sample obtained from a reservoir during scanning thereof;
  (b) optionally at least one of a core gamma scanner, a spectral gamma ray scanner, an XRF scanner, or a XRD scanner;
  (c) optionally at least one of an SEM and an FIB-SEM for imaging a selected representative subsample or a selected portion thereof; and
  (d) one or more computer systems operable to (i) receive image output of the multi-energy X-ray CT scanner, the core gamma scanner, the spectral gamma ray scanner, the XRF scanner, the XRD scanner, the SEM, and the FIB-SEM, and to (ii) obtain bulk density and photoelectric effect index for the sample using CT values obtained for voxels in the sample from the multi-energy X-ray CT scan, (iii) estimate at least one mineral property using data obtained from at least one of a core gamma scan, a spectral gamma ray scan, and XRF analysis, or an XRD analysis of the sample, (iv) determine at least one sample property by combining the bulk density, photoelectric effect index, and said at least one mineral property, and (v) output the results to at least one device to display, print, or store results of the computations.
26. The system of any preceding or following embodiment/feature/aspect, wherein the system is a mobile system.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be exemplary of the present invention.

EXAMPLES

Data and Workflow.

FIGS. 1-11 show results of applying a method of the present invention to an exemplary shale core sample obtained from a well. The depth plots of the multiple energy X-ray imaging-derived bulk density ($\rho_b$), the effective atomic number ($Z_{Eff}$), and the photoelectric effect index ($P_e$) for an exemplary core under examination are shown in FIGS. 1A-C. $P_e$ was computed from $Z_{Eff}$ with Equation (1) as $$P_e=(Z_{Eff}/10)^{3.6}. \quad (1)$$

Figure 1B:
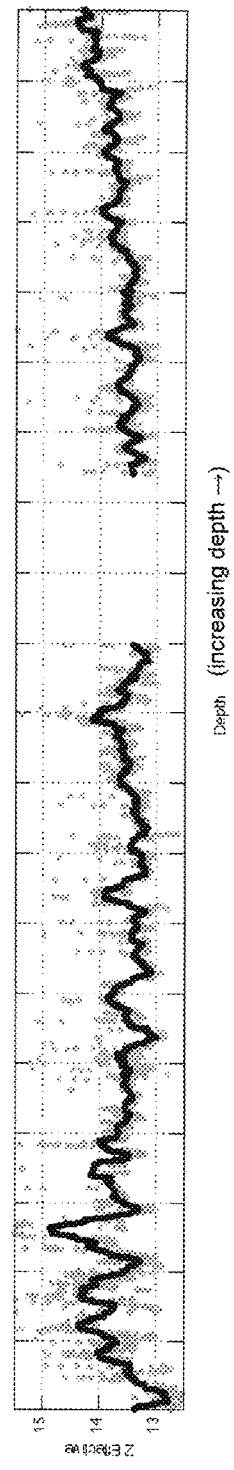
Figure 1C:
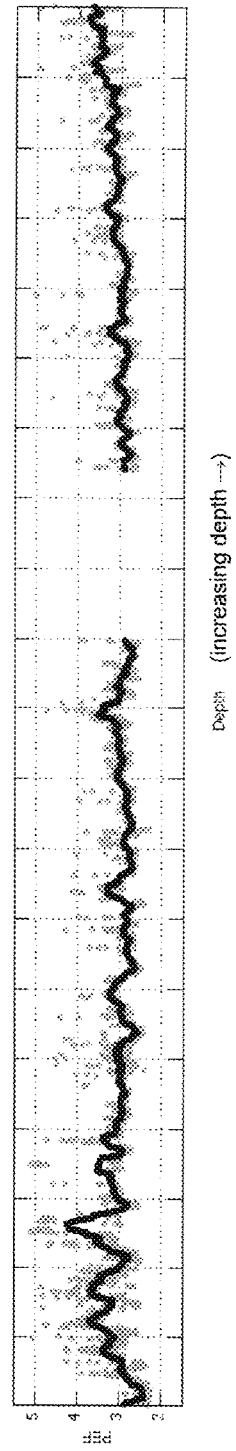

As indicated, in FIGS. 1A-C, depth plots are shown of the multiple energy X-ray imaging-derived bulk density, effective atomic number, and photoelectric effect index for the core under examination. The black symbols are for the variables smoothed by a running arithmetic average filter with the window length 50 samples.

The multiple energy X-ray imaging-derived mineralogy was computed by assuming that the measured $P_e$ is a linear interpolation between two end members, e.g., one end member is a mixture of quartz and illite (end member "1" whose $P_e$ is $P_{e1}$) while the other end member is pure calcite (end member "2" whose $P_e$ is $P_{e2}$), wherein $$P_e=f_1P_{e1}+(1-f_1)P_{e2}, \quad (2)$$

where $f_1$ is the volume fraction of the first mineralogical end member in the mineral mixture.

It follows from Equation 2 that $$f_1=(P_{e2}-P_e)/(P_{e2}-P_{e1}). \quad (3)$$

In the upper part of the core, it is assumed that the first end member is the mixture of 30% illite and 70% quartz, while in the lower part, it is the mixture of 60% illite and 40% quartz. The second end member in both intervals is pure calcite. The $P_e$ values for these end members are listed in Table 1.

Table 1 shows photoelectric effect index numbers for the end-member mineralogy assumed here.

TABLE 1

| End Member Mineralogy | Photoelectric Effect Index Number |
|---|---|
| 30% Illite + 70% Quartz (PEF1, upper interval < 9485 ft) | 2.28 |
| 60% Illite + 40% Quartz (PEF1, lower interval > 9485 ft) | 2.77 |
| 100% Calcite (PEF2, entire depth range) | 5.08 |

Then, it is next assumed that the fraction of quartz in the first end member is $f_{Q1}$ while the fraction of illite is $f_{I1} = 1 - f_{Q1}$. Then, Equation 3 can be resolved to obtain the volume fractions of the three minerals in a sample as $$f_Q = f_{Q1} f_1, f_I = (1 - f_{Q1}) f_1, f_C = 1 - f_1, \quad (4)$$

where now $f_Q$ is the volume quartz content in the entire sample, $f_I$ is the same for illite, and $f_C$ is the same for calcite.

$$f_Q + f_I + f_C = f_{Q1} f_1 + (1 - f_{Q1}) f_1 + 1 - f_1 = 1.$$

Finally, Equations 3 and 4 can be combined to obtain $$f_Q = f_{Q1} \frac{P_{e2} - P_e}{P_{e2} - P_{e1}}, \quad (5)$$
$$f_I = (1 - f_{Q1}) \frac{P_{e2} - P_e}{P_{e2} - P_{e1}},$$
$$f_C = 1 - \frac{P_{e2} - P_e}{P_{e2} - P_{e1}}.$$

Figure 2:
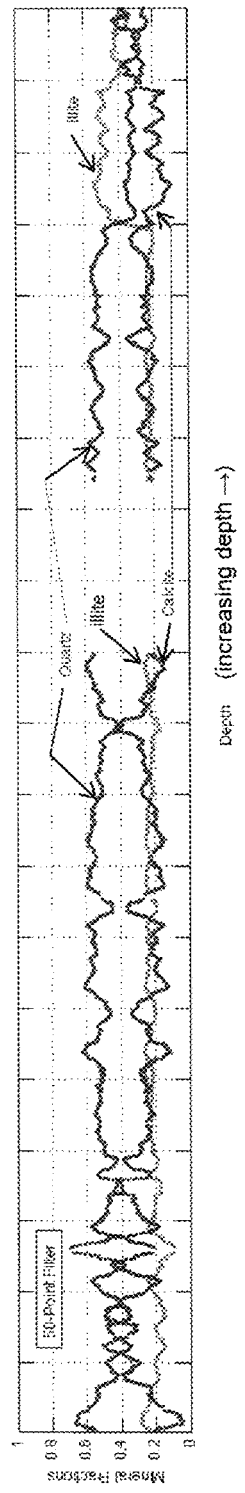
FIG. 2 shows curves of resulting mineral fractions of calcite, quartz and illite determined according to Equation 5 herein that are plotted versus depth according to an example of the present application. The curves are smoothed by a 50-point filter.
Figure 3:
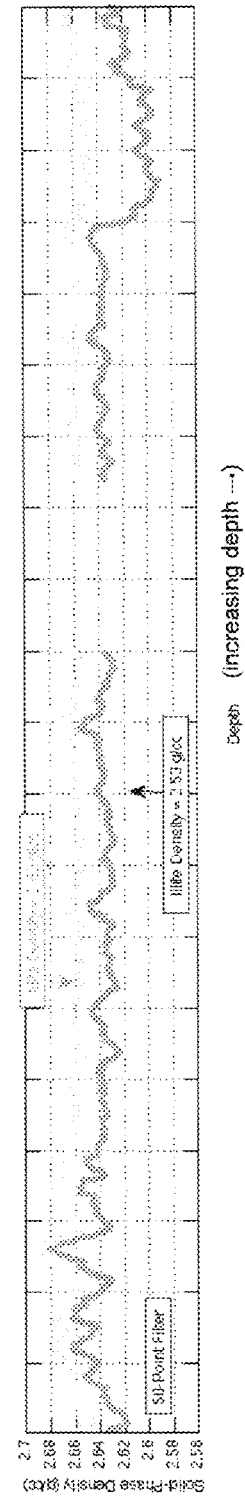
FIG. 3 shows curves of the density of the solid phase of the rock computed from fractions and densities of pure quartz, illite, and calcite determined with Equation 6 herein plotted versus depth, and an alternate curve for a different assumed density of illite ($\rho_1=2.63$ g/cc instead of 2.53) plotted in the same figure, according to an example of the application.

The resulting mineral fractions (smoothed) are plotted versus depth in FIG. 2. In FIG. 2, mineral fractions, according to Equation 5, versus depth, are shown wherein the plots for calcite; quartz; and illite are identified. The curves in FIG. 2 are smoothed by a 50-point filter.

The density of the solid phase ($\rho_s$) was computed from these mineral fractions as $$\rho_s = f_Q \rho_Q + f_I \rho_I + f_C \rho_C, \quad (6)$$

where the densities of pure quartz, illite, and calcite are, respectively, $\rho_Q = 2.65$ g/cc, $\rho_I = 2.53$ g/cc, and $\rho_C = 2.71$ g/cc. It is plotted versus depth in FIG. 3, which shows solid phase density, wherein the curves are smoothed by a 50-point filter.

Figure 4:
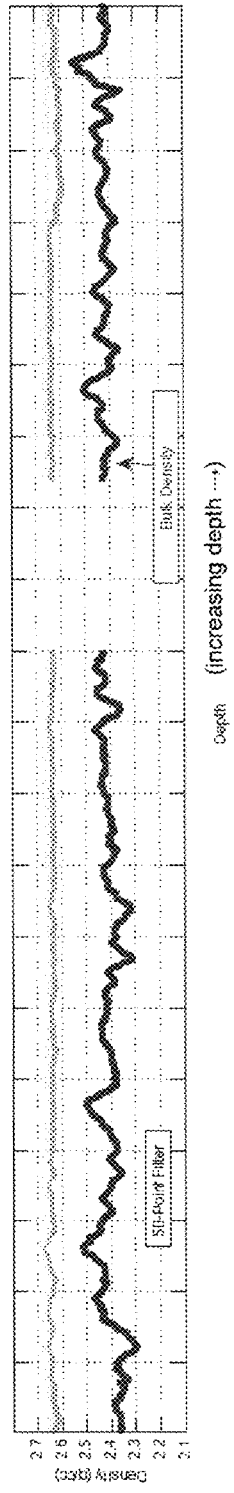
FIG. 4 shows the same data as plotted in FIG. 3 with multiple energy X-ray imaging bulk density curve (smoothed) added for reference according to an example of the application.

An alternative curve for assumed $\rho_I = 2.63$ g/cc is plotted in the same figure. The same data are re-plotted in FIG. 4 but with multiple energy X-ray imaging bulk density curve given for reference. That is, FIG. 4 is the same as FIG. 3 but with the smoothed bulk density curve (lower plot) added for reference.

Porosity Computations.

Figure 5:
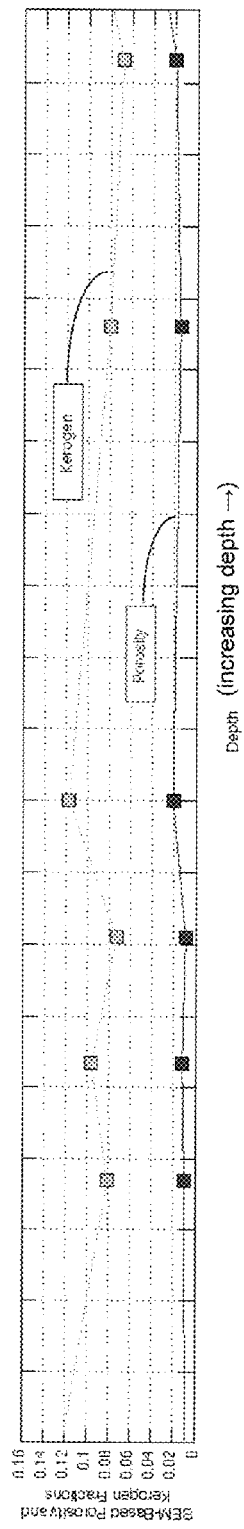
FIG. 5 shows 2D-SEM-based porosity and kerogen (volume) fractions for ten plugs according to an example of the application.

FIG. 5 shows the 2D-SEM-based porosity and kerogen (volume) fractions ten plugs selected for this illustration. The plotted values are also listed in Table 2. In FIG. 5, the SEM-based porosity (lower plot) and kerogen volume fraction (upper plot), wherein the connecting lines are simple linear interpolations.

As indicated, Table 2 shows SEM-based kerogen and porosity fractions for the ten plugs under examination. The different indicated depths in Table 2 correspond to a different one of the indicated ten plugs. The values of the depths in Table 2 are normalized wherein "X" is the same number.

TABLE 2

| Depth (ft) | Kerogen | Porosity | Sum |
|---|---|---|---|
| X379.25 | 0.1250 | 0.0100 | 0.1350 |
| X385.50 | 0.1540 | 0.0080 | 0.1620 |
| X418.50 | 0.0810 | 0.0100 | 0.0910 |
| X426.70 | 0.0960 | 0.0120 | 0.1080 |
| X435.50 | 0.0730 | 0.0090 | 0.0820 |
| X445.00 | 0.1170 | 0.0210 | 0.1380 |
| X478.00 | 0.0800 | 0.0150 | 0.0950 |
| X496.58 | 0.0680 | 0.0200 | 0.0880 |
| X508.70 | 0.1050 | 0.0450 | 0.1500 |
| X526.50 | 0.1130 | 0.0100 | 0.1230 |

The measured bulk density is the sum of the densities contributed by the mineral solid, kerogen, and the fluid in the pores. If it is assumed that the pores are empty, the latter term becomes zero. Hence, $$\rho_b = X_s \rho_s + X_k \rho_k, \quad (7)$$

where $X_s$ is the volume fraction of solid mineral in the entire rock and $X_k$ is the same for kerogen. Also, $\rho_k$ is the density of kerogen, and the density of the solid phase is $\rho_s$. It is necessary that $$X_s + X_k + \phi = 1, \quad (8)$$

where $\phi$ is the porosity.

Next, by combining Equation 7 and 8, porosity is $$\phi = [\rho_s - \rho_b - X_k(\rho_s - \rho_k)]/\rho_s. \quad (9)$$

Figure 6A:
FIGS. 6A-B show multiple energy X-ray imaging-based ("ME-Xray-I") porosity as computed from Equation 9 herein using the solid-phase density curves shown in FIG. 3 and assuming the kerogen density is 1.00 g/cc, wherein the plot of FIG. 6A is for the solid-phase density computed using the illite density 2.53 g/cc while the plot of FIG. 6B is for the alternative solid-phase density curve computed using the illite density of 2.63 g/cc, and wherein the SEM-based porosity is shown as stars, according to an example of the present application.
Figure 6B:
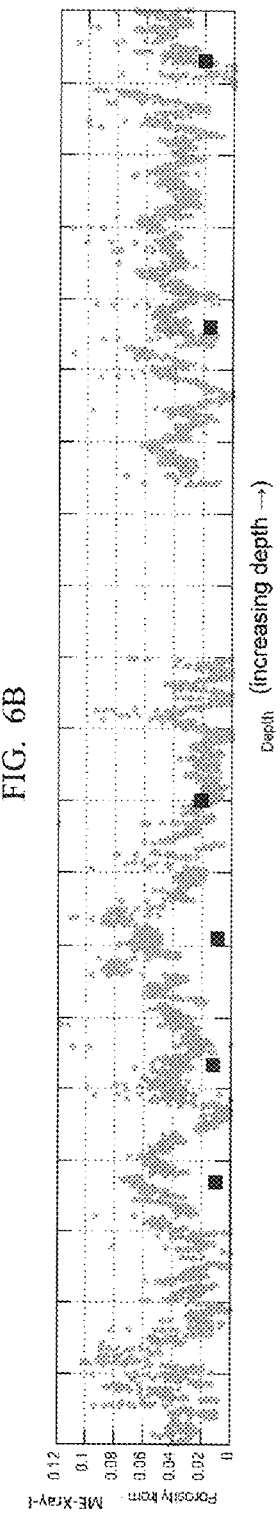

It can then be assumed that $X_k$ in the entire interval under examination is given by the interpolation curve shown in FIG. 5. Then, by using Equation 9, the porosity can be computed by using both $\rho_s$ curves shown in FIG. 3. The results are compared with the SEM-derived porosity in FIGS. 6A-B assuming that the density of kerogen $\rho_k = 1.00$ g/cc. The porosity values that fall below zero are corrected to be exactly zero. FIGS. 6A-B show, multiple energy X-ray imaging-based porosity as computed from Equation 9 using the solid-phase density curves displayed in FIG. 3 and assuming the kerogen density 1.00 g/cc. The plot in FIG. 6A is for the solid-phase density computed using the illite density 2.53 g/cc while the plot in FIG. 6B is for the alternative solid-phase density curve computed using the illite density 2.63 g/cc. The SEM-based porosity is shown as stars.

Brittleness Index.

The computation of the brittleness index B can be based on the ability to quantify the three components in the mineral phase: clay, quartz, and calcite. In this case, the clay is illite.

First, the effective bulk and shear moduli of the solid matrix ($K_s$ and $G_s$, respectively) were computed from Hill's average of the moduli of the three individual mineral components as $$K_s = \frac{1}{2}\left[\left(\frac{f_Q}{K_Q} + \frac{f_C}{K_C} + \frac{f_I}{K_I}\right)^{-1} + (f_Q K_Q + f_C K_C + f_I K_I)\right], \quad (10)$$
$$G_s = \frac{1}{2}\left[\left(\frac{f_Q}{G_Q} + \frac{f_C}{G_C} + \frac{f_I}{G_I}\right)^{-1} + (f_Q G_Q + f_C G_C + f_I G_I)\right],$$

where $f_Q$, $f_C$, and $f_I$ are the volume fractions of quartz, calcite, and illite in the matrix, respectively (as defined earlier in this document); $K_Q$, $K_C$, and $K_I$ are the bulk moduli of these individual minerals, and $G_Q$, $G_C$, and $G_I$ are their shear moduli. These individual elastic moduli are listed in Table 3. Alternatively, any method of computing the effective bulk and shear moduli of the mineral face can be used, such as Hashin-Shtrikman bounds.

Table 3 shows elastic moduli and densities of individual minerals used in brittleness computations.

TABLE 3

| Mineral | Density (g/cc) | Bulk Modulus (GPa) | Shear Modulus (GPa) |
|---|---|---|---|
| Quartz | 2.65 | 36.6 | 45.0 |
| Calcite | 2.71 | 76.8 | 32.0 |
| Illite | 2.53 | 25.5 | 16.3 |

The next step is to compute the Young's modulus $E_s$ (MPa) and Poisson's ratio $v_s$ of the mineral matrix by using standard elasticity equations $$E_s = \frac{9K_s G_s}{3K_s + G_s}, \quad v_s = \frac{3K_s - 2G_s}{2(3K_s + G_s)}. \quad (11)$$

These elastic moduli are our proxies for the static moduli traditionally used in brittleness computations.

Next, new variables $E_B$ and $v_B$ are introduced by ad-hoc normalizing $E_s$ and $v_s$ as follows $$E_B = E_s/50, v_B = v_s/0.8, \quad (12)$$

where $E_s$ is in GPa. Next, the brittleness index B is introduced as $$B = 47.467(E_B + v_B). \quad (13)$$

These specific numbers were selected to produce maximum B=100 which occurs at about 40% quartz, 60% calcite and zero illite. B=98.833 for pure calcite; 94.697 for pure quartz; and 52.302 for pure illite. The value "47.467" in equation (13) may be approximated as about 47.

Figure 7A:
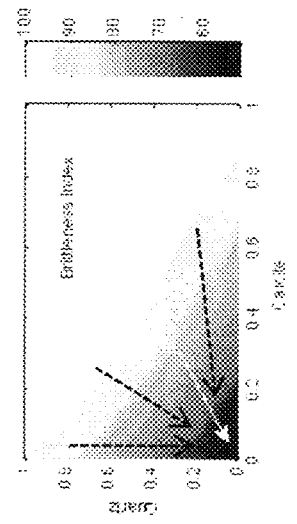
FIGS. 7A-C show diagrams for the Brittleness Index value "B" of Equation 13 herein versus the mineral fractions as computed according to the method, with the brittleness index shown by greyscale shading versus the fractions of calcite and illite (FIG. 7A), quartz and illite (FIG. 7B), and calcite and quartz (FIG. 7C), wherein the solid white arrow in each plot shows the direction of the increasing fraction of the third mineral and the hatched black arrows in each plot indicate the direction in which the brittleness index values gradually transition in the plot from higher values near 100 to lower values approaching 55, according to an example of the present application.
Figure 7B:
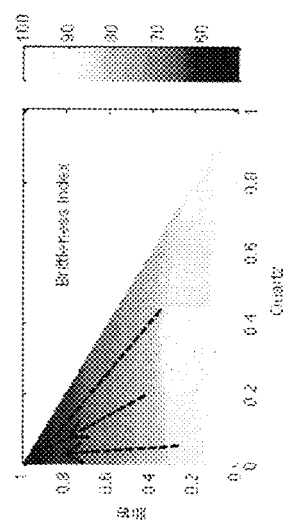
Figure 7C:
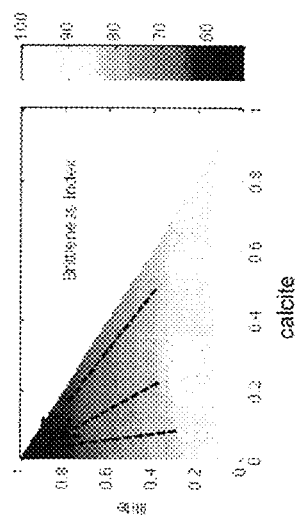

Diagrams for B versus the mineral fractions as computed according to this method are shown in FIGS. 7A-C. In FIGS. 7A-C, the brittleness index is shown by shading versus the fractions of calcite and illite (FIG. 7A), quartz and illite (FIG. 7B), and calcite and quartz (FIG. 7C). The solid arrow in each plot shows the direction of the increasing fraction of the third mineral, and the hatched black arrows in each plot indicate the direction in which the brittleness index values gradually transition in the plot from higher values near 100 to lower values approaching 55.

Figure 8A:
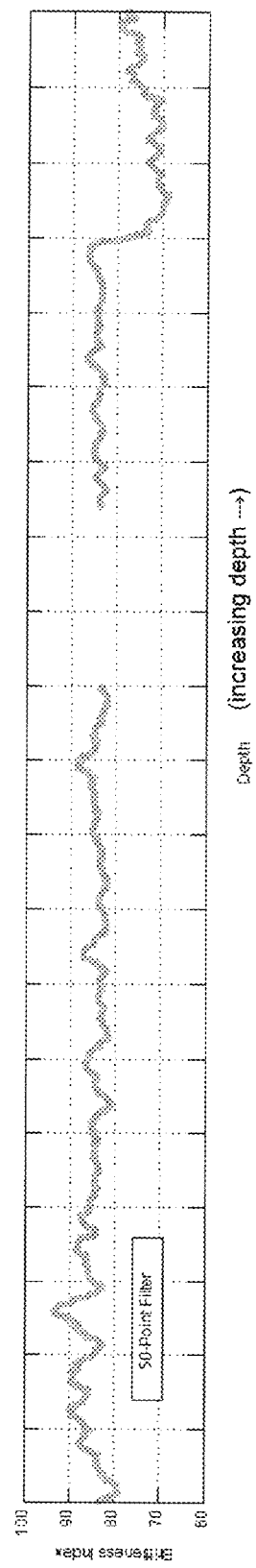
FIGS. 8A-B show the brittleness index computed by the method for the multiple energy X-ray imaging log under examination, wherein the Brittleness index shown in FIG. 8A is computed from the multiple energy X-ray imaging mineralogy (mineral fractions) shown in FIG. 6B for corresponding depths, according to an example of the present application.
Figure 8B:
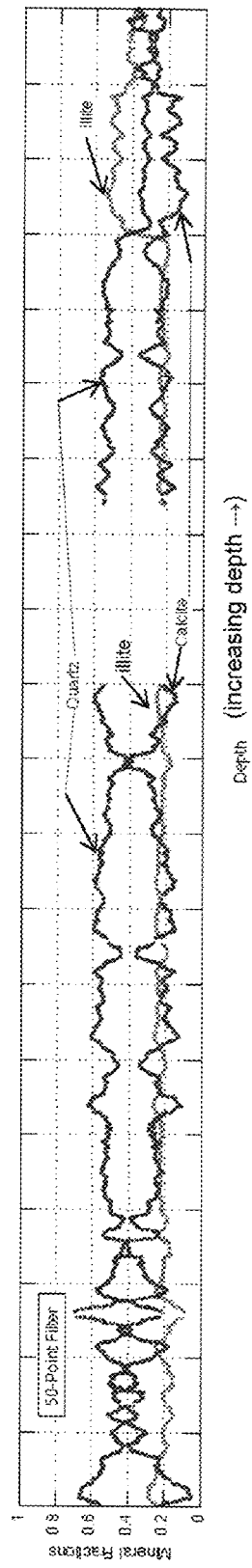

The brittleness index computed by this method for the multiple energy X-ray imaging log under examination is shown in FIGS. 8A-B. These figures show Brittleness index (FIG. 8A) computed from the multiple energy X-ray imaging mineralogy (FIG. 8B).

Porosity and Permeability.

The method of estimating the permeability k of a 2D segmented image is based, for example, on computing the porosity $\phi$ and specific surface area s of the image and then applying the Kozeny-Carman equation $$k = 0.5\phi^3/(s^2\tau^2), \quad (14)$$

where the tortuosity $\tau$ is assumed to be a function of porosity. Its upper bound is $$\tau_+ = 0.4038(1 + 1/\phi) \quad (15)$$

while its lower bound is $$\tau_- = 0.4470\phi^{-1.2}. \quad (16)$$

Equation 14 combined with Equation 15 will give the lower permeability bound while Equation 14 combined with Equation 16 will give the upper permeability bound.

Of course, the specific surface area is not available from multiple energy X-ray imaging. To bypass this problem, a theoretical parameter is introduced, the grain size d and it is assumed that this grain size in a depth interval is consistent with that computed on a representative segmented 2D slice from its porosity and specific surface area as $$d = 6(1-\phi)/s. \quad (17)$$

As a result, Equation 14 becomes $$k = \frac{d^2}{72} \frac{\phi^3}{(1-\phi)^2 \tau^2}. \quad (18)$$

Figure 9A:
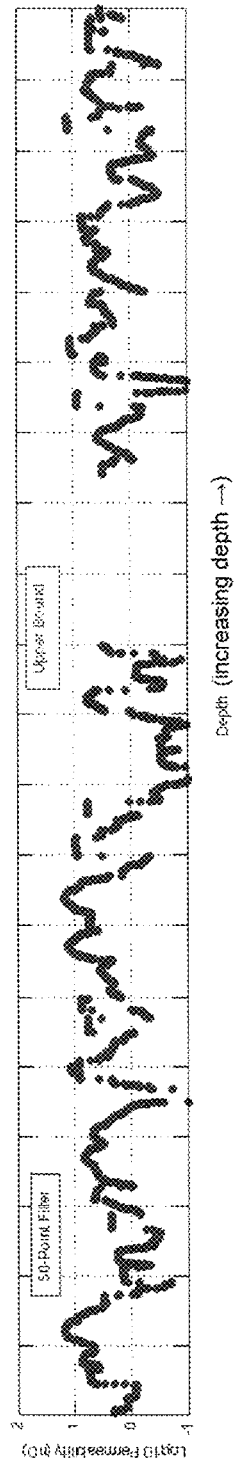
FIGS. 9A-C that show permeability (decimal logarithm) versus depth from multiple energy X-ray imaging with the upper bound shown in FIG. 9A, the lower bound is shown in FIG. 9B, and the mean is shown in FIG. 9C, according to an example of the present application.
Figure 9B:
Figure 9C:
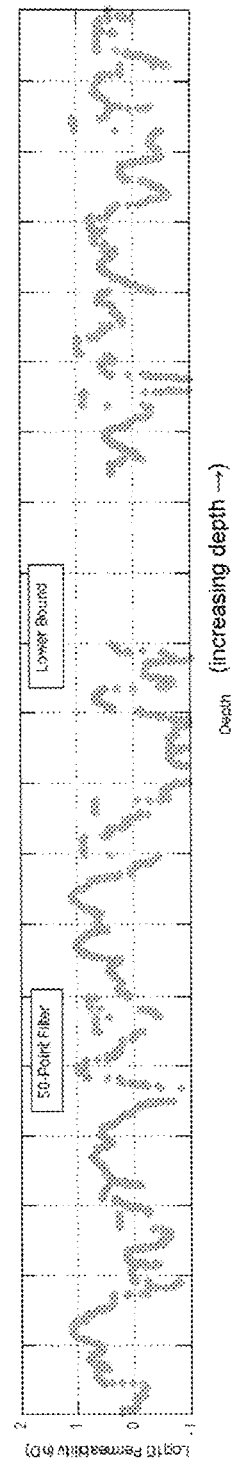

The grain size d computed on several 2D SEM images from a well varies between 1.0e-7 and 2.0e-7 m ($1 \times 10^{-7}$ to $2 \times 10^{-7}$ m). In the present example we selected d=1.5e-7 m=150 nm for the entire interval under examination. Equation 18 together with Equations 15 and 16 were applied to the entire interval by using the porosity curve shown in FIG. 6A. The results are shown in FIGS. 9A-C for the upper and lower permeability bounds as well as for their mean. In FIGS. 9A-C, permeability (decimal logarithm) versus depth from multiple energy X-ray imaging is shown for the upper bound (FIG. 9A), the lower bound (FIG. 9B)), and the mean (FIG. 9C). The permeability can be determined by any other empirical or theoretical permeability equation that uses porosity, grain size or pore size or specific surface area.

Summary Attribute.

Figure 10A:
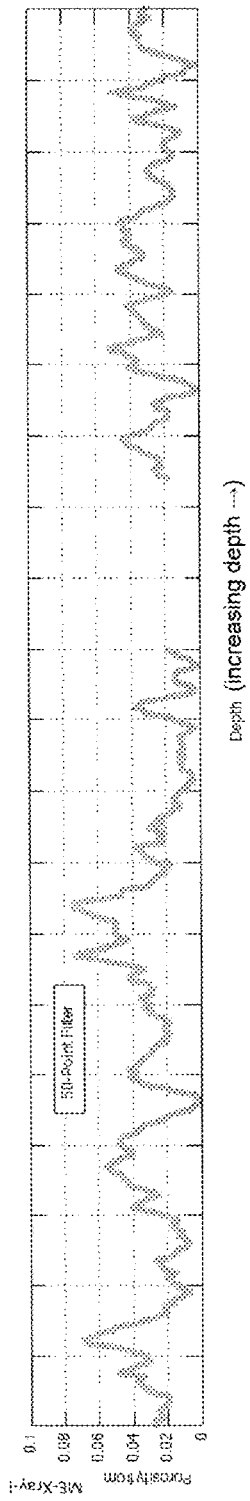
FIGS. 10A-C show plots of the smoothed porosity, permeability, and brittleness curves derived from the multiple energy X-ray imaging ("ME-Xray-I") data, wherein the porosity is shown in FIG. 10A, permeability (decimal logarithm) is shown in FIG. 10B, and the brittleness index versus depth is shown in FIG. 10C, according to an example of the present application.
Figure 10B:
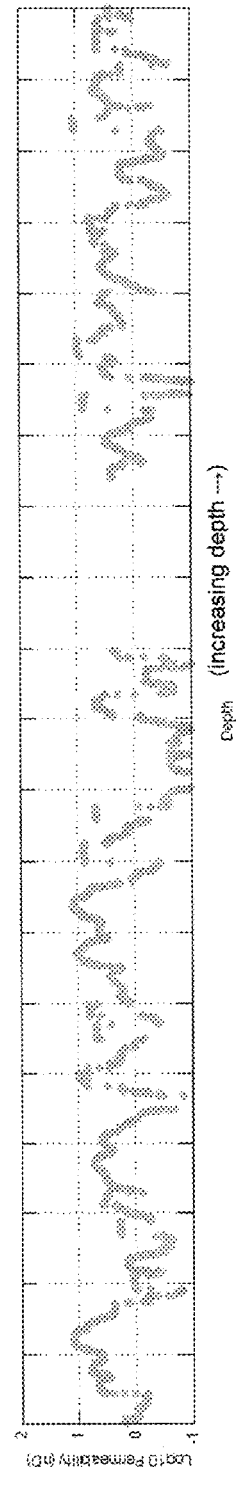
Figure 10C:
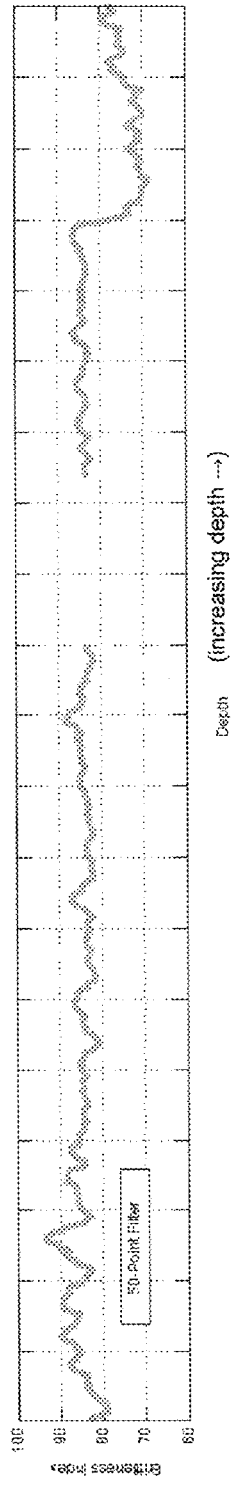

In FIGS. 10A-C, the smoothed porosity, permeability, and brittleness curves derived here from the multiple energy X-ray imaging data are plotted. In FIGS. 10A-C, the porosity (FIG. 10A), permeability—decimal logarithm (FIG. 10B), and the brittleness index (FIG. 10C), are plotted versus depth.

A reservoir quality attribute is created that increases with increasing porosity, permeability, and brittleness as, e.g., $$A = 1 + \phi \cdot \log(k) \cdot B/20. \quad (19)$$

Figure 11:
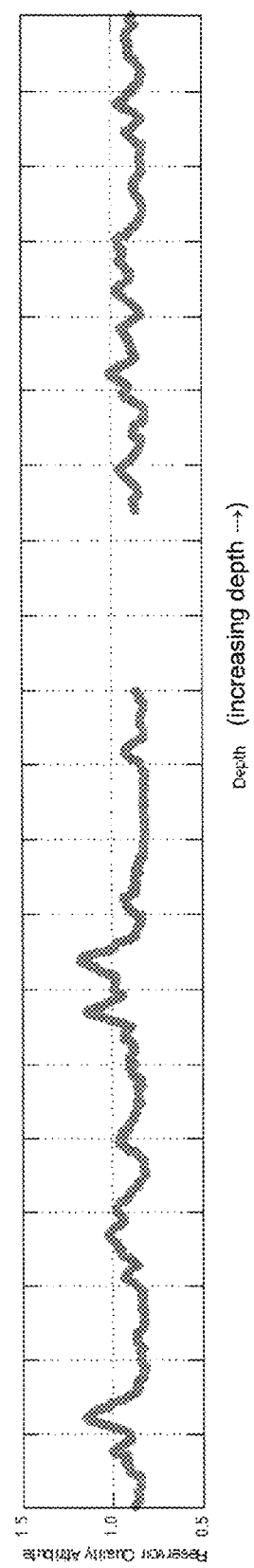
FIG. 11 shows a reservoir quality attribute determined according to Equation 19 herein according to an example of the present application.

FIG. 11 shows a reservoir quality attribute determined according to Equation 19.

Figure 12:
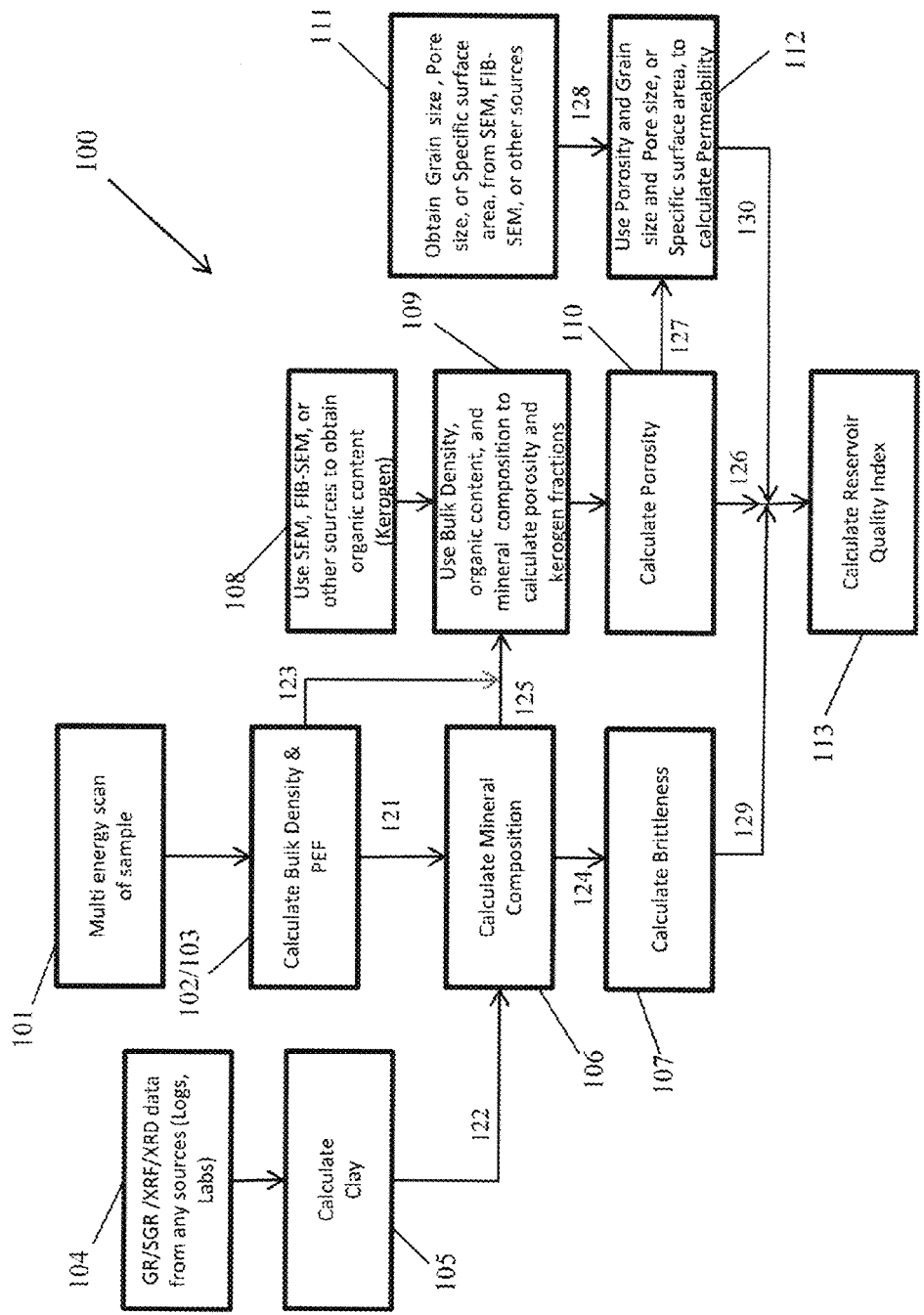
FIG. 12 shows a process diagram of a reservoir evaluation method according to the present application.

FIG. 12 shows a process diagram of a reservoir evaluation method of the present application. Steps 101-113 of the method shown as process flow 100 are illustrated in FIG. 12. Various process flow stream options are included and available, such as indicated by 121-130. With respect to steps 108, 109, and 110, for example, it is noted that from SEM or FIB-SEM or other sources, porosity and organic content can be obtained, though usually the organic content is more reliable. In view of this reason, the organic content is illustrated herein as used to calculate porosity, although the method is not limited to this approach. The opposite can be done, for example, wherein the organic content is calculated by using the porosity from the SEM or FIB-SEM or other sources.

Figure 13:
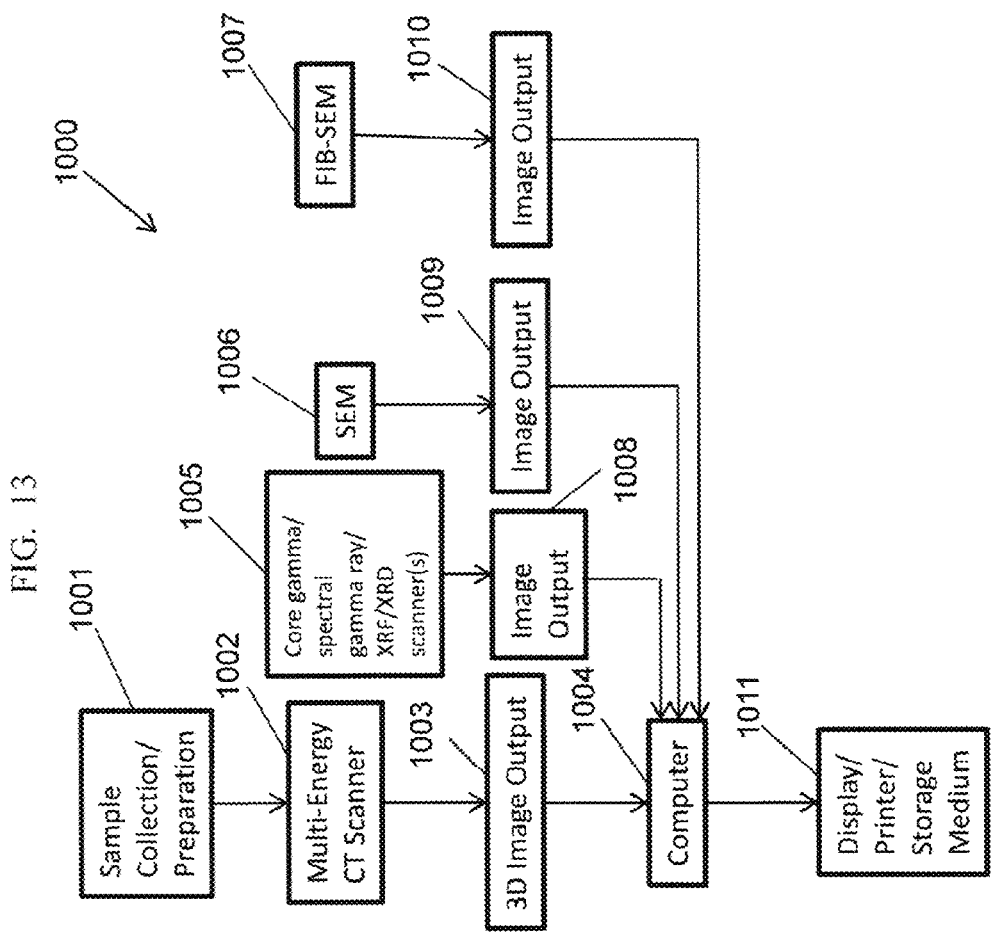
FIG. 13 shows a system according to an example of the present application.

The present invention also relates to a system for providing estimation of reservoir properties, such as formation brittleness, porosity, organic material content, and/or permeability without need of detailed lab physical measurements or destruction of the sample, such as according to the processes shown in FIGS. 1-12. As illustrated in FIG. 13, for example, the system 1000 can include a sample collection and/or preparation station 1001, at least one multi-energy CT scanner 1002, optionally a core gamma scanner, a spectral gamma ray scanner, X-ray fluorescence (XRF) scanner, and/or X-ray diffraction (XRD) scanner 1005, and optionally at least one of an SEM 1006 and a FIB-SEM 1007. One or more computer systems 1004 can be provided for capture and processing of image data from the multi-energy CT scanner 1002, and if used, the core gamma scanner, spectral gamma ray scanner, XRF scanner, XRD scanner 1005, the SEM 1006 and/or the FIB-SEM 1007, and to output the results to at least one output device 1011 to display, print, or store results, or any combinations thereof, of the image processing and computations of a method of the present application. The computer system 1004 can be configured, for example, to receive image output from at least one or all of the image output 1003 from the multi-energy CT scanner 1002, output 1008 from core gamma scanner, spectral gamma ray scanner, XRF scanner and/or XRD scanner 1005 if used, image output 1009 from the SEM 1006 if used, and image output 1010 from the FIB-SEM 1007 if used. The computer programs used for image analysis and the computations can be stored, as a program product, on at least one non-transitory computer usable storage medium (e.g. a hard disk, a flash memory device, a compact disc, a magnetic tape/disk, or other media) associated with at least one processor (e.g., a CPU) which is adapted to run the programs, or may be stored on an external non-transitory computer usable storage medium which is accessible to the computer processor. The system of the present application can be located and used off-site or on-site with respect to where the samples are obtained. If used off-site, samples can be transported to the location where the system is located. If used on-site, the system optionally can be used in a mobile enclosure such as a trailer, van, motor coach, or similar device, such that it can be transported to a well site or other sample source location and analyses run on-site. The system of the present application can be a stationary, semi-stationary, or mobile system.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of evaluating a reservoir, comprising:
    (a) performing a multi-energy X-ray CT scan of a sample at a depth interval at two or more different energy levels;
    (b) obtaining bulk density and photoelectric effect index for the sample using CT values obtained for voxels in the sample from the multi-energy X-ray CT scan;
    (c) estimating at least one mineral property using data obtained from at least one of a core gamma scan, a spectral gamma ray scan, an X-ray fluorescence (XRF) analysis, or an X-ray diffraction (XRD) analysis of the sample; and
    (d) determining at least one sample property by combining the bulk density, photoelectric effect index, and said at least one mineral property.

2. The method of claim 1, wherein the at least one mineral property comprises total clay content.

3. The method of claim 1, further comprising performing a core gamma scan or a spectral gamma ray scan on the sample prior to step (c).

4. The method of claim 1, wherein the estimating of the at least one mineral property comprises using data of at least one of a gamma ray or a spectral gamma ray scan of the sample to estimate total clay content, and calculating a mineral composition of the sample using the estimate of total clay content and the photoelectric effect index.

5. The method of claim 4, further comprising determining brittleness index of the sample using the mineral composition.

6. The method of claim 5, wherein the determining of the brittleness index comprises determining the brittleness index from elastic properties of the solid calculated from the mineral composition.

7. The method of claim 5, wherein the brittleness index is in positive numerical relationship to Young's modulus and Poisson's ratio.

8. The method of claim 5, wherein the brittleness index is in positive linear numerical relationship to Young's modulus and Poisson's ratio.

9. The method of claim 4, further comprising using an organic content obtained for the sample and bulk density and mineral composition to calculate porosity.

10. The method of claim 9, wherein obtaining the organic content of the sample comprises determining the organic content using SEM, CT scan, pyrolysis, FTIR, or FIB-SEM.

11. The method of claim 9, further comprising:
    a) obtaining grain size or pore size, or specific surface area; and
    b) calculating permeability of the sample using porosity, or grain size or pore size or specific surface area.

12. The method of claim 9, further comprising calculating a reservoir quality index of the sample using brittleness and porosity.

13. The method of claim 11, further comprising calculating a reservoir quality index of the sample using brittleness, porosity, and permeability.

14. The method of claim 1, wherein the sample is a core.

15. The method of claim 1, wherein the sample is a set of drill cuttings.

16. The method of claim 1, wherein the sample is a plug.

17. A method for evaluating a reservoir, comprising:
    (a) performing a multi-energy X-ray CT scan of a sample at a depth interval at two or more different energy levels;
    (b) obtaining bulk density and photoelectric effect index for the sample using CT values obtained for voxels in the sample from the multi-energy X-ray CT scan;
    (c) using data of at least one of a gamma ray scan, a spectral gamma ray scan, an X-ray fluorescence (XRF) analysis, or an X-ray diffraction (XRD) analysis of the sample to estimate total clay content;
    (d) calculating a mineral composition of the sample using the estimate of total clay content and the photoelectric effect index;
    (e) determining brittleness index of the sample using the mineral composition;
    (f) determining kerogen fraction;
    (g) determining porosity of the sample using the bulk density, mineral composition, and the kerogen fraction;
    (h) estimating permeability of the sample using the porosity and grain size, pore size, or specific surface area; and
    (i) determining a reservoir quality index by combining the brittleness index, porosity, and permeability.

18. The method of claim 17, wherein reservoir quality index is in positive numerical relationship with the brittleness index, porosity, and permeability.

19. The method of claim 17, wherein the determining of the mineral composition of the sample using the photoelectric effect index comprises scaling the photoelectric effect index as a linear interpolation between first and second mineralogical end members of the sample, wherein the first mineralogical end member is a mixture of a first mineral and a second mineral wherein the first mineralogical end member has a $P_e$ which is $P_{e1}$, and the second mineralogical end member is a third mineral which has a $P_e$ which is $P_{e2}$, wherein a volume fraction $f_1$ of the first mineralogical end member in a mineral mixture of the sample is calculated as $f_1=(P_{e2}-P_e)/(P_{e2}-P_{e1})$.

20. The method of claim 19, wherein the first, second, and third minerals are different minerals from each other.

21. The method of claim 19, wherein the first mineral is quartz, the second mineral is illite, and the third mineral is pure calcite.

22. The method of claim 21, wherein the fraction of quartz in the first mineralogical end member is $f_{Q1}$ and the fraction of illite is $f_{I1}=1-f_{Q1}$, and wherein volume fractions of the first mineral, the second mineral, and the third mineral in the sample as an entirety are calculated respectively as $f_Q=f_{Q1}f_1$, $f_I=(1-f_{Q1})f_1$, $f_C=1-f_1$, wherein $f_Q+f_I+f_C$ is 1.

23. The method of claim 17, wherein the determining of the porosity $\phi$ of the sample is calculated as $\phi=[\rho_s-\rho_b-X_k(\rho_s-\rho_k)]/\rho_s \cdot \rho_b=X_s\rho_s+X_k\rho_k$, where $X_s$ is volume fraction of solid mineral in the entire sample and $X_k$ is volume fraction for kerogen in the entire sample and $X_s+X_k+\phi=1$, wherein measure bulk density obeys the relationship $\rho_b=X_s\rho_s+X_k\rho_k$, wherein $\rho_s$ is density of the solid phase and $\rho_k$ is density of kerogen.

24. The method of claim 17, wherein the sample is a core or a set of drill cuttings or a plug.

25. A system for evaluating a reservoir, comprising:
(a) a multi-energy X-ray CT scanner having a stage capable of holding a sample obtained from a reservoir during scanning thereof;
(b) optionally at least one of a core gamma scanner, a spectral gamma ray scanner, an XRF scanner, or a XRD scanner;
(c) optionally at least one of an SEM and an FIB-SEM for imaging a selected representative subsample or a selected portion thereof; and
(d) one or more computer systems operable to (i) receive image output of the multi-energy X-ray CT scanner, the core gamma scanner, the spectral gamma ray scanner, the XRF scanner, the XRD scanner, the SEM, and the FIB-SEM, and to (ii) obtain bulk density and photoelectric effect index for the sample using CT values obtained for voxels in the sample from the multi-energy X-ray CT scan, (iii) estimate at least one mineral property using data obtained from at least one of a core gamma scan, a spectral gamma ray scan, an XRF analysis, or an XRD analysis of the sample, (iv) determine at least one sample property by combining the bulk density, photoelectric effect index, and said at least one mineral property, and (v) output the results to at least one device to display, print, or store results of the computations.

26. The system of claim 25, wherein the system is a mobile system.

* * * * *